United States Patent [19]

Wagner

[11] 4,400,350

[45] Aug. 23, 1983

[54] PALLADIUM DENTAL ALLOY

[75] Inventor: Armin C. Wagner, Mine Hill, N.J.

[73] Assignee: W. C. Heraeus GmbH, Hanau am Main, Fed. Rep. of Germany

[21] Appl. No.: 427,283

[22] Filed: Sep. 29, 1982

[51] Int. Cl.³ .................................................. C22C 5/04
[52] U.S. Cl. ................................................... 420/464
[58] Field of Search ........................ 420/464, 465, 463

[56] References Cited

U.S. PATENT DOCUMENTS 2,132,116 10/1938 Kiepe ..................................... 420/464
2,222,544 11/1940 Spanner et al. ....................... 420/464

FOREIGN PATENT DOCUMENTS 1,111,111 of 0000 .

Primary Examiner—W. Stallard

Attorney, Agent, or Firm—Frishauf, Holtz, Goodman & Woodward

[57] ABSTRACT

A homogeneous fine grained palladium alloy consisting essentially of

|    | Weight Percent |
|----|----------------|
| Pd | 70–82          |
| Au | 0.1–10         |
| In | 5–10           |
| Cu | 2–5            |
| Ga | 0.5–5          |
| Sn | 0.5–5          |
| Co | 0.9–2.7        |
| Re | 0.01–0.3       | and between 0.08 and 0.25% of at least one metal selected from the group consisting of Ru and Ir.

5 Claims, No Drawings

PALLADIUM DENTAL ALLOY

The present invention provides a palladium alloy useful as a dental alloy in the manufacture of dentures and other prosthetic devices.

BACKGROUND OF THE INVENTION

Dental alloys must have a unique combination of properties. They should have high strength and tarnish resistance. They should have good castability, molding, working and burnishing characteristics so that they may be readily manufactured. They should also be compatible with other dental materials such as porcelain which they contact and have a suitable coefficient of expansion. The alloy must also have satisfactory color characteristics. It should not be discolored or cause discoloration of other dental materials with which it is in contact during the manufacturing process and later in service. The dental alloys must also meet the demanding requirements of non-toxicity.

Gold alloys have been the traditional dental alloys. Because of the high cost of such alloys and the ever more demanding technical specifications for such alloys, there has long been a need for improved and less expensive dental alloys. Many base metal alloys, such as nickel-chromium and cobalt-chromium have been proposed and found unsatisfactory. Palladium alloys have been proposed, some of which also contained silver or gold, see for example, U.S. Pat. Nos. 3,134,671; 3,819,366; 4,179,288; 4,261,744; and 4,319,877. Nos. 4,261,744 and 4,319,877 disclose palladium alloys which contain indium, tin and cobalt.

It is the object of the present invention to provide an improved dental alloy which has good working characteristics for manufacture, good service characteristics, and which is relatively inexpensive.

SUMMARY OF THE INVENTION

The present invention provides a homogeneous palladium alloy containing the metals listed in the following Table. The Table also lists the broad and preferred range in which each metal is present in the alloy.

|  | Broad Range % | Preferred Range % |
|---|---|---|
| Pd | 70–82 | 74–80 |
| Au | 0.1–10 | 2–5 |
| In | 5–10 | 6–8 |
| Cu | 2–5 | 2.5–3.5 |
| Ga | 0.5–5 | 2.5–4.5 |
| Sn | 0.5–5 | 2.5–3.5 |
| Co | 0.9–2.7 | 0.63–2.25 |
| Re | 0.01–0.3 | 0.07–0.25 |
| Ru and/or Ir | 0.08–0.25 | 0.04–0.06 for each |

The palladium alloys of the present invention are one phase homogeneous alloys having fine grain size which are strong and tough. They have good casting characteristics and good molding characteristics. Their melting point is generally in the range of 1200°–1260° C. which permits use of commercially available casting machines and also conventional high heat investment casting molds.

In the as cast condition, they are relatively soft, for example, from about 185 to about 235 Vickers. They can be cold deformed up to 75% and even more with a strain relief heat treatment. There is no brittleness. The alloys have high elongation, i.e. up to about 37% in the soft condition and as much as 36% in the hard condition. This permits burnishing to correct off-dimensions which may have occurred during the molding technique to bring the casting to the correct size and/or shape. The alloys have low density relative to that of the gold base alloys, i.e. about 11.3–11.9.

Heat treatment of the alloy to the temperature at which porcelain is fired when used to form the dental prosthetic device followed by cooling in air causes the alloy to harden. Successive firings and coolings, e.g., the usual four or five firings which form the conventional process of manufacture of dental prosthetic devices comprising the palladium alloy and porcelain bonded thereto will harden the alloy to the range of 250–280 Vickers.

The palladium alloy must have surface characteristics which permit the formation of a good bond to the dental porcelain. This requires some oxide formation at the surface of the palladium alloy. However, the alloy should have low oxidation characteristics so that only the amount of oxide necessary for good bonding occurs. Excess formation of oxide is undesired because it results in discoloration of the prosthetic dental device and may adversely affect the bonding characteristics.

The color of interface of the dental porcelain with the surface of the palladium alloy of the present invention caused by the oxide is an initial light grey which changes to greyish-golden during consecutive firings (which also function as heat treatments) during the four or five firings at temperatures between about 960° and 996° F. which are carried out during the conventional manufacture of porcelain-containing prosthetic dental devices. The end product has no dicoloration caused by oxide formation.

The palladium alloy after firing is tough, hard, takes a good polish, and has an expansion coefficient which is closely matched to that of the dental porcelain which is important to achieve and maintain a good bond between the palladium alloy and the porcelain.

The tin, gallium and indium function to lower the melting point of the alloy and to increase the coefficient of expansion. They also increase the strength and hardness of the alloy.

The gold and the gallium function to increase the cast-ability of the alloy.

The copper acts as a filler and regulates the amount of oxide at the surface of the alloy to provide the desired degree of oxidation which is sufficient to achieve good bonding characteristics without causing discoloration.

The rhenium, ruthenium and iridium function as grain refiners. The cobalt functions to lower the melting point of the alloy and to increase the expansion coefficient. Preferably, the cobalt acts as a carrier for the rhenium.

The palladium alloys of the present invention are prepared by melting the components in the manner in which noble metal and other palladium dental alloys are prepared. The highest technical grade of each of the components is used. The component (with the exception of gold) are pre-vacuum melted. The palladium alloy of the present invention is then prepared by vacuum melting the components until a homogeneous alloy is formed at a temperature starting above about the melting point of palladium (1554° C.) and then adding lower melting point components and lowering the temperature to about 1300° C. and then casting at about 1350°–1400° C. Because of the small amounts of certain of the components and particularly the rhenium, ruthenium and iridium, it is preferable that these components be preformed into a master alloy with one or more of the other components of the alloy. The master alloy or alloys are then utilized as the source of these components which are added in small amounts. Preforming into a master alloy or enveloping particles of other metals such as gallium or tin with foil of another metal is also preferred.

It is particularly preferred to add the rhenium in the form of a master alloy with cobalt, prferably a master alloy containing between about 90 and 95% cobalt with a preferred composition of about 90% cobalt and 10% rhenium.

The ruthenium and/or iridium are preferably added in the form of a master alloy containing between about 90 and 95% palladium and a total of between about 5 and 10% of ruthenium and/or iridium. The preferred master alloys contain about 90% palladium with the remainder ruthenium and/or iridium. The preferred master alloy contains ruthenium and iridium in about equal amounts.

The present invention is further illustrated in the following examples. All parts and percentages in the specification are by weight.

The compositions of the exemplified palladium alloys of the present invention are set forth in the following Table.

|  | Example No. | | |
|---|---|---|---|
|  | 1 | 2 | 3 |
| Pd | 79.9 | 73.9 | 77.9 |
| Au | 2 | 10 | 5 |
| In | 7 | 5 | 9 |
| Cu | 3 | 4 | 2 |
| Ga | 4 | 2.5 | 3 |
| Sn | 3 | 2 | 2 |
| Co | 0.9 | 2.25 | 0.9 |
| Re | 0.1 | 0.25 | 0.1 |
| Ru | 0.05 | 0.05 | 0.05 |
| Ir | 0.05 | 0.05 | 0.05 |

The properties of the exemplified alloys are set forth in the following Table.

| Example No. | Vickers Hardness | | Density g/cm$^3$ | Melting Range °C. |
|---|---|---|---|---|
|  | Soft | Hard |  |  |
| 1 | 235 | 275 | 11.3 | 1240–1280 |
| 2 | 215 | 260 | 11.9 | 1200–1260 |
| 3 | 185 | 250 | 11.5 | 1225–1270 |

What is claimed is:

1. A homogeneous fine grained palladium alloy consisting essentially of

|  | Weight Percent |
|---|---|
| Pd | 70–82 |
| Au | 0.1–10 |
| In | 5–10 |
| Cu | 2–5 |
| Ga | 0.5–5 |
| Sn | 0.5–5 |
| Co | 0.9–2.7 |
| Re | 0.01–0.3 | and between 0.08 and 0.25% of at least one metal selected from the group consisting of Ru and Ir.

2. The alloy of claim 1 containing between 74 and 80% Pd, between 2 and 5% Au, between 6 and 8% In, between 2.5 and 3.5% Cu, between 2.5 and 4.5% Ga, between 2.5 and 3.5% Sn, between 0.63 and 2.25% Co and between 0.07 and 0.25% Rh.

3. The alloy of claim 1 or 2 containing Ru and Ir, each in an amount between 0.04 and 0.125%.

4. The alloy of claim 3 consisting essentially of

|  | Weight Percent |
|---|---|
| Pd | 79.9 |
| Au | 2 |
| In | 7 |
| Cu | 3 |
| Ga | 4 |
| Sn | 3 |
| Co | 0.9 |
| Re | 0.1 |
| Ru | 0.05 |
| Ir | 0.05 |

5. The alloy of claim 1 or 2 containing Ru and Ir, each in an amount between 0.04 and 0.06%.

* * * * *